United States Patent [19]

Thomas, Jr. et al.

[11] 3,998,827

[45] Dec. 21, 1976

[54] 6-AMINO-4-(SUBSTITUTED PIPERIDINO)-1,2-DIHYDRO-1-HYDROXY-2-IMINOPYRIMIDINES

[75] Inventors: Richard C. Thomas, Jr.; Harry Harpootlian, both of Portage, Mich.

[73] Assignee: The Upjohn Company, Kalamazoo, Mich.

[22] Filed: Feb. 27, 1975

[21] Appl. No.: 553,799

Related U.S. Application Data

[63] Continuation of Ser. No. 132,153, April 7, 1971, abandoned.

[52] U.S. Cl. .................... 260/256.4 C; 260/239.1; 260/247.2 B; 260/256.4 N; 260/256.5 R; 260/256.4 B; 424/251; 260/247.5 D

[51] Int. Cl.² .................................... C07D 239/34

[58] Field of Search ............ 260/256.4 C, 247.2 B, 260/247.5 C

[56] References Cited

UNITED STATES PATENTS

| | | | |
|---|---|---|---|
| 3,382,248 | 5/1968 | Anthony et al. | 260/256.4 C |
| 3,461,461 | 8/1969 | Anthony et al. | 260/256.4 C |
| 3,639,667 | 2/1972 | Ursprung et al. | 260/256.4 C |

*Primary Examiner*—Donald G. Daus
*Assistant Examiner*—James H. Turnipseed
*Attorney, Agent, or Firm*—Bruce Stein; Carl A. Randles, Jr.; Roman Saliwanchik

[57] ABSTRACT

6-Amino-1,2-dihydro-1-hydroxy-2-iminopyrimidines, their carboxyacylated counterparts, and the corresponding acid addition salts thereof are disclosed. These compounds, useful inter alia as antihypertensive agents, are substituted in the 4-position and optionally in the 5-position, the substituent in the 4-position being oxygen bearing secondary or tertiary amino moiety.

4 Claims, No Drawings

6-AMINO-4-(SUBSTITUTED PIPERIDINO)-1,2-DIHYDRO-1-HYDROXY-2-IMINOPYRIMIDINES

This is a continuation of application Ser. No. 132,153, filed Apr. 7, 1971, and now abandoned.

BRIEF DESCRIPTION OF THE INVENTION

This invention relates to novel compositions of matter and to methods for producing them. In particular, this invention relates to novel 1,2-dihydro-1-hydroxypyrimidines of the formula:

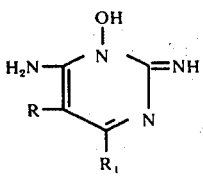

wherein $R_1$ is an oxygen bearing primary or secondary amino moiety of the formula:

wherein $R_3$ and $R_4$ taken separately are hydrogen, lower alkyl, lower alkenyl, lower aralkyl, lower cycloalkyl, lower hydroxy, alkoxy- or acyloxy-substituted alkyl, lower hydroxy-, alkoxy-, or acyloxy-substituted aralkyl and lower hydroxy-, alkoxy- or acyloxy-substituted cycloalkyl, with the proviso that both $R_3$ and $R_4$ are not hydrogen and that at least one of $R_3$ or $R_4$ is substituted by hydroxy-, alkoxy- or acyloxy-substituent; or taken together with the nitrogen is aziridinyl, azetidinyl, pyrrolidinyl, piperidino, hexahydroazepinyl, heptamethyleneimino, octamethyleneimino, morpholino, and 4-lower-alkylpiperazinyl, each of said heterocyclic moieties having attached as substituents on carbon atoms thereof zero to 3 lower alkyl, inclusive, and, in addition one or two hydroxy, lower alkoxy or lower acyloxy groups which may be attached to a carbon of the heterocyclic ring or of a substituent side chain alkyl group. When $R_1$ is not a heterocyclic moiety $R_3$ and $R_4$ can be alike or different. When $R_1$ is a heterocyclic moiety, the alkyls, or hydroxy-, lower alkoxy-, or lower acyloxy-substituted alkyls which can be attached thereto can all be different or any two or all of them can be alike.

R in Formula I is hydrogen, lower alkyl, lower alkenyl, lower alkoxyalkyl, lower cycloalkyl, lower aryl, lower aralkyl, lower alkaryl, lower alkaralkyl, lower alkoxy-aralkyl, lower haloaralkyl, chlorine, or bromine.

The novel 1,2-dihydro-1-hydroxypyrimidines of this invention can be represented by formulas other than Formula I. For example, with regard to Formula I, among such other formulas are:

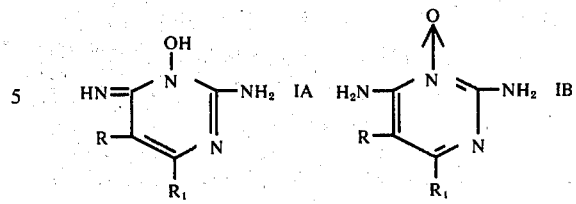

Compounds of Formula IA and IB are tautomeric with compounds of Formula I. For convenience, reference will be made hereinafter only to Formula I. It is to be understood, however, that the novel compounds of this invention are likely to be mixtures of tautomeric forms, the compositions of which are dependent on such factors as the nature of R and $R_1$ and the environment. In some instances, one form or another may predominate.

Examples of lower alkyl are methyl, ethyl, propyl, butyl, pentyl, hexyl, heptyl, octyl, and isomeric forms thereof. Examples of lower alkenyl are allyl, 1-methylallyl, 2-methylallyl (methallyl), 2-butenyl (crotyl), 3-butenyl, 1,2-dimethylallyl, 1,1,-dimethylallyl, 2-ethylallyl, 1-methyl-2-butenyl, 2-methyl-2-butenyl, 3-methyl-2-butenyl, 3-pentenyl, 2,3-dimethyl-2-butenyl, 1,1,2-trimethylallyl, 1,3-dimethyl-2-butenyl, 1-ethyl-2-butenyl, 4-methyl-2-pentenyl, 2-ethyl-2-pentenyl, 4,4-dimethyl-2-pentenyl, 2-heptenyl, 2-octenyl, 5-octenyl, 1,4-dimethyl-4-hexenyl, and the like. Examples of lower alkoxyalkyl are 2-methoxyethyl, 2-ethoxyethyl, 2-butoxyethyl, 2-hexyloxyethyl, 2-octyloxyethyl, 2-methoxypropyl, 3-methoxypropyl, 3-propoxypropyl, 2-methoxybutyl, 3-ethoxybutyl, 4-butoxybutyl, 2-ethoxyhexyl, 3-methoxy-3-methylpentyl, 4-methoxyoctyl, and the like. Examples of lower cycloalkyl are cyclopropyl, 2-methylcyclopropyl, 2,2-dimethylcyclopropyl, 2,3-diethylcyclopropyl, 2-butylcyclopropyl, cyclobutyl, 2-methylcyclobutyl, 3-propylcyclobutyl, 2,3,4-triethylcyclobutyl, cyclopentyl, 2,2-dimethylcyclopentyl, 3-pentylcyclopentyl, 2-tert-butylcyclopentyl, cyclohexyl, 4-tert-butylcyclohexyl, 3-isopropylcyclohexyl, 2,2-dimethylcyclohexyl, cycloheptyl, cyclooctyl, and the like. Examples of lower aryl are phenyl, 1-naphthyl, and 2-naphthyl. Examples of lower alkaryl are o-tolyl, m-tolyl, p-tolyl, m-ethylphenyl, p-tert-butylphenyl, the isomeric forms of xylyl, the isomeric forms of trimethylphenyl, 4-methyl-1-naphthyl, 6-propyl-2-naphthyl, 2,4,5,7-tetramethyl-1-naphthyl, and the like. Examples of lower aralkyl are benzyl, phenethyl, 1-phenylethyl, 2-phenylpropyl, 4-phenylbutyl, 6-phenylhexyl, 5-phenyl-2-methylpentyl, 1-naphthylmethyl, 2-(1-naphthyl)ethyl, 2-(2-naphthyl)ethyl, and the like. Examples of lower alkaralkyl are o-tolylmethyl, m-tolylmethyl, p-tolylmethyl, 4-tert-butylphenylmethyl, 2-(p-tolyl)ethyl, 1-(m-tolyl)ethyl, 3-(o-ethylphenyl)propyl, 4-methyl-2-naphthylmethyl, 6-tert-butyl-2-naphthylmethyl, and the like. Examples of lower alkoxyaralkyl are o-methoxybenzyl, m-methoxybenzyl, p-methoxybenzyl, 2-(m-methoxyphenyl)ethyl, 3-(p-ethoxyphenyl)propyl, 4-(p-tert-butoxyphenyl)butyl, 4-methoxy-1-naphthylmethyl, and the like. Examples of lower haloaralkyl are o-chlorobenzyl, m-fluorobenzyl, p-bromobenzyl, 2-(m-iodophenyl)ethyl, 2,4-dichlorobenzyl, 6-bromo-1-naphthylmethyl, 4-(p-chlorophenyl)butyl, and the like. Examples of lower hydroxyalkyl are hydroxymethyl, 1-hydroxyethyl, 2-hydroxyethyl, 1-hydroxypropyl, 2-hydroxypropyl, 3-hydroxypropyl, 2-hydroxybutyl, and isomeric forms thereof.

Examples of lower acyloxyalkyl are acetoxymethyl, propionoxymethyl, 2-butyroxypropyl, and 3-acetoxybutyl.

Examples of hydroxyaralkyl are α-hydroxybenzyl, 2-hydroxy-2-phenylethyl, 2-hydroxy-3-phenylpropyl, and 2-hydroxy-2-phenylpropyl.

Examples of acyloxyaralkyl are α-acetoxybenzyl, 2-acetoxy-2-phenylethyl, 2-propionoxy-3-phenylpropyl, and 2-butyroxy-2-phenylpropyl.

Examples of hydroxycycloalkyl are 2-hydroxycyclohexyl, 3-hydroxycyclopropyl, 4-hydroxymethylcyclohexyl, and 3-hydroxy-4-methylcyclohexyl.

Examples of alkoxycycloalkyl are 2-methoxycyclohexyl, 3-ethoxycyclopropyl, 4-propoxymethylcyclohexyl, and 3-ethoxy-4-methylcyclohexyl.

Examples of acyloxycycloalkyl are 2-acetoxycyclohexyl, 3-butyroxycyclopropyl, 4-acetoxymethylcyclohexyl, 3-propionoxy-4-methylcyclohexyl.

Examples of heterocyclic moieties within the scope of $R_1$ are 2-hydroxymethylaziridinyl, 2-methyl-3-hydroxymethylaziridinyl, 2-methoxymethylaziridinyl, 2-methyl-3-acetoxymethylaziridinyl, 3-hydroxyazetidinyl, 2-methyl-3-methoxyazetidinyl, 3-hydroxypyrrolidinyl, 3-methoxy-4-methylpyrrolidinyl, 2,6-dimethyl-3-methoxypyrrolidinyl, 3-hydroxypiperidino, 4-hydroxypiperidino, 3,4-dihydroxypiperidino, 2-hydroxymethylpiperidino, 3-hydroxymethylpiperidino, 2-(2-hydroxyethyl)piperidino, 3-(1-hydroxyethyl)piperidino, 2,2,6,6-tetramethyl-4-hydroxypiperidino, 4-hydroxy-4-methylpiperidino, 4-methyl-4-propoxypiperidino, 4-butoxyethylpiperidino, 3-acetoxypiperidino, and 4-propionoxypiperidino.

In each of the above examples of heterocyclic moieties, the free valence, and hence the point of attachment to a carbon atom of the pyrimidine ring, is at the heterocyclic nitrogen atom.

The novel 1,2-dihydro-1-hydroxypyrimidines of Formula I are amines, and exist in the non-protonated or free base form, or in the protonated or acid addition salt form, depending on the pH of the environment. They form stable protonates, i.e., mono- or diacid addition salts, on neutralization with suitable acids, for example, hydrochloric, hydrobromic, sulfuric phosphoric, nitric, acetic, benzoic, salicylic, glycolic, succinic, nicotinic, tartaric, maleic, malic, pamoic, methanesulfonic, cyclohexanesulfamic, picric, and lactic acids, and the like. These acid addition salts are useful for upgrading or purifying the free bases. The free bases are useful as acid acceptors in neutralizing undesirable acidity or in absorbing an acid as it is formed in a chemical reaction, for example, a dehydrohalogenation reaction in which hydrogen and chlorine, bromine, or iodine are removed from vicinal carbon atoms.

The novel Formula I compounds form salts with fluosilicic acid which are useful as mothproofing agents according to U.S. Pat. Nos. 1,915,334 and 2,075,359. They also form salts with thiocyanic acid which condense with formaldehyde to form resinous materials useful as pickling inhibitors according to U.S. Pat. Nos. 2,425,320 and 2,606,155.

The Formula I 1,2-dihydro-1-hydroxypyrimidines of this invention also form salts with penicillins. These salts have solubility characteristics which cause them to be useful in the isolation and purification of penicillins, particularly benzyl penicillin. Said salts can be formed either by neutralization of the free base form of a compound of Formula I with the free acid form of a penicillin, or by a metathetical exchange of the anion of an acid addition salt of a Formula I compound, for example, the chloride ion of a hydrochloride with the anionic form of a penicillin.

The novel Formula I 1,2-dihydro-1-hydroxypyrimidines also form carboxyacylates on treatment with carboxyacylating agents, for example, carboxylic acid anhydrides and carboxylic acid chlorides. These carboxyacylates can be single compounds or mixtures of compounds depending on such factors as the nature of the 1,2-dihydro-1-hydroxypyrimidine reactant, the carboxyacylating agent, and the reaction conditions.

Carboxyacylates obtained from Formula I 1,2-dihydro-1-hydroxypyrimidines can be represented by the formula:

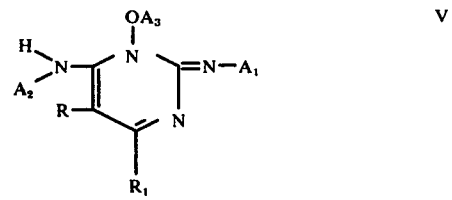

V wherein R and $R_1$ are as defined above. $A_1$, $A_2$, and $A_3$ are each selected from the group consisting of hydrogen and carboxyacyl, with the proviso that at least one of $A_1$ and $A_2$ is carboxyacyl.

The carboxyacylates of Formula V can be used for upgrading a Formula I 1,2-dihydro-1-hydroxypyrimidine free base. The latter can be transformed to a carboxyacylate, the carboxyacylate purified by conventional techniques, e.g., recrystallization or chromatography, and the purified carboxyacylate deacylated, advantageously by alcoholysis.

The dihydropyrimidine carboxyacylates of Formula V can be represented by other formulas. As for Formula I compounds, these Formula V carboxylates are likely to be mixtures of tautomeric forms, the compositions of which are dependent on such factors as the nature of the substituents and the carboxyacyl moieties, and the environment. In some instances, one form or another may predominate. Formula V is used for convenience, and the other tautomeric forms are not excluded.

Carboxyacylates of Formula V are amines and exist in either the nonprotonated (free base) form or the protonated (acid addition salt) form depending upon the pH of the environment. They form stable protonates on neutralization with suitable strong acids, for example, hydrochloric acid, sulfuric acid, phosphoric acid, perchloric acid, and the like. These acid addition salts are useful for upgrading or purifying the carboxyacylate free bases.

The novel compounds of this invention, including the free bases of Formula I, the acid addition salts thereof, the carboxyacylates of Formula V, and the acid addition salts thereof possess pharmacological activity. For example, they are orally and parenterally active in birds and mammals, including man, as antihypertensive agents having vasodilatory activity, are are useful for lowering blood pressure and for the treatment of shock. They are also useful as antifertility agents, as antiviral agents, as anti-inflammatory agents, and as central nervous system stimulants. The compounds of this invention have the added advantage over those of U.S. Pat. No. 3,461,461 in that they bear oxygen substituents on R or $R_1$ providing a means for more rapid conjugation and excretion when the compounds are administered. This gives better control of the desired pharmacologic activity, particularly when administered to diseased patients.

These compounds also cause electrolyte and water retention in laboratory animals such as rats and dogs, and hence are useful to produce laboratory animals with larger than normal amounts of sodium ions, potassium ions, chloride ions, and water. Such animals are useful in pharmacological research, for example, in screening compounds for possible diuretic activity and in studying the action of known diuretics.

The compounds of Formula I, for example, wherein R is hydrogen or lower alkyl and $R_1$ is 3-hydroxy- or 4-hydroxypiperidine are especially useful as antihypertensive agents in mammals, including man.

The novel 1,2-dihydro-1-hydroxypyrimidines of Formula I are produced by mixing a compound of the formula:

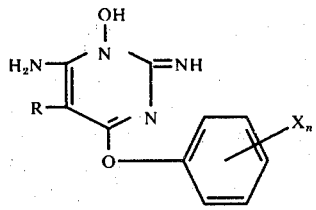

VI wherein X is fluorine, chlorine, or bromine, and $n$ is 0 to 3, inclusive, and wherein R is as defined above, with an amine of the formula $R_1H$, wherein $R_1$ is as defined above. The phenoxy moiety of the Formula VI reactant is displaced by the $R_1$ moiety of the amine.

The reaction between a Formula VI 1,2-dihydro-1-hydroxy-4-phenoxypyrimidine and an amine of formula $R_1H$, wherein $R_1$ is as defined above, to produce a Formula I 1,2-dihydro-1-hydroxypyrimidine is carried out by mixing those two reactants and heating the mixture in the range about 100° to about 200° C., preferably in the range about 125° to about 175° C. At least one molecular equivalent of the amine should be mixed with each molecular equivalent of the pyrimidine reactant. It is usually advantageous to use an excess of the amine, for example, about 2 to about 20 molecular equivalents or even more of amine per molecular equivalent of the pyrimidine, the excess amine then acting as a diluent. An inert organic diluent can also be present in the reaction mixture. Especially suitable for that purpose are dialkylformamides, particularly those where the dialkyl substituents are the same as those of the displacing amine, and alkanols.

When the reactant amine has a relatively low boiling point and is likely to escape from the reaction vessel during heating, it is advantageous to use a closed reaction vessel, for example, a heavy-wall, sealed, glass tube or a closed metal autoclave for the heating step.

A reaction time of about one to about 20 hours is usually required. The desired displacement reaction usually takes place more rapidly at higher temperatures than at lower. Moreover, when the phenoxy moiety has 2 or 3 halogen substituents, i.e., when $n$ in Formula VI is 2 or 3, the displacement usually takes place more rapidly and at a lower temperature than when fewer or no halogen is present. In the latter instances, especially when no halogen is present in the phenoxy moiety, the displacement reaction is often accelerated by adding sodium or potassium metal to the reaction mixture. Preferably, about one atomic equivalent of the alkali metal is added per molecular equivalent of the pyrimidine reactant. Addition of a catalytic amount of a Lewis acid such as ferric chloride with the alkali metal will also often accelerate the displacement reaction or make feasible a lower reaction temperature. About 0.01 to 0.001 molecular equivalents of ferric chloride per atomic equivalent of alkali metal is usually a suitable catalytic amount.

The compounds of Formula I are also produced from 4-chloropyrimidine-N-oxides of the formula

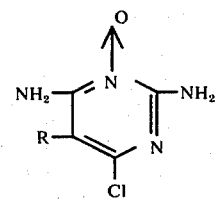

VII by displacement of the chlorine with an amine $R_1H$ where R and $R_1$ are as herein defined.

Primary amines of formula R'H which can be used as starting reactants for the above processes are 6-amino-1-hexanol, 2-amino-1-methoxypropane, 4-(aminomethyl)cyclohexanemethanol, 2-amino-2-methyl-1,3-propanediol, 2-amino-2-methyl-1-propanol, 5-amino-1-pentanol, 2-amino-1-phenylethanol, 2-amino-1-phenyl-1,3-propanediol, 3-amino-1,2-propanediol, 1-amino-2-propanol, 2-amino-1-propanol, 3-amino-1-propanol, N,N-bis(2,2-diethoxyethyl)amine, ethanolamine, 2-ethoxyethylamine, 3-isopropoxypropylamine, 3-(2-methoxyethoxy)propylamine, 2-methoxyethylamine, 3-methoxypropylamine, 2-acetoxyethylamine, and 2-amino-1-acetoxypropane.

Examples of suitable starting secondary amines of Formula R'H are 1-benzylamino-2-propanol, 2-benzylamino-1-propanol, 3-benzylamino-1-propanol, N-benzylethanolamine, N,N-bis(2,2-diethoxyethyl)methylamine, bis-1,2-ethoxyethylamine, 2-(n-butylamino)ethanol, 2-(t-butylamino)ethanol, 2-cyclohexylaminoethanol, methylaminoacetaldehyde dimethylacetal, 2-methylaminoethanol, 4-benzyl-4-hydroxypiperidine, 3-hydroxypiperidine, 4-hydroxypiperidine, 2-(2-piperidine)ethanol, 2-piperidinemethanol, 3-piperidinemethanol, 2,2,6,6-tetramethyl-4-piperidinol, 1-(3-piperidinyl)ethanol, 4-(n-butoxyethyl)piperidine, 3-methoxypiperidine, 4-acetoxypiperidine, and cis- and trans-3,4-dihydroxpiperidine.

The desired Formula I 1,2-dihydro-1-hydroxypyrimidine can be isolated from the reaction mixture by the methods outlined in U.S. Pat. No. 3,461,461 or by the usual methods of chromatography, liquid-liquid countercurrent extraction, simple solvent extraction and/or fractional crystallization. The isolated pyrimidine can then be purified, if desired, by conventional techniques, for example, recrystallization from a suitable solvent or mixture of solvents, or by chromatography. Alternatively, an acid addition salt, e.g., the hydrochloride or acid phosphate of the pyrimidine product can be prepared, purified by recrystallization, and then, if desired, reconverted to the free base in the usual manner.

The 1,2-dihydro-1-hydroxypyrimidines of Formula I are transformed to monoacid and diacid addition salts by neutralization with appropriate amounts of the corresponding inorganic or organic acid, examples of which are given above. These transformations can be carried out by a variety of procedures known to the art to be generally useful for the preparation of amine acid addition salts. The choice of the most suitable procedure will depend on a variety of factors including convenience of operation, economic considerations, and particularly the solubility characteristics of the Formula I amine, the acid, and the acid addition salt. If the acid is soluble in water, the basic compound of Formula I can be dissolved in water containing either one or two equivalent amounts of the acid, and thereafter, the water can be removed by evaporation. If the acid is soluble in a relatively nonpolar solvent, for example, diethyl ether or diisopropyl ether, separate solutions of the acid and the basic Formula I compound in such a solvent can be mixed in equivalent amounts, whereupon the acid addition salt will usually precipitate because of its relatively low solubility in the nonpolar solvent. Alternatively, the basic Formula I compound can be mixed with the acid in the presence of a solvent of moderate polarity, for example, a lower alkanol, a lower alkanone, or a lower alkyl ester of a lower alkanoic acid. Examples of these solvents are ethanol, acetone, and ethyl acetate, respectively. Subsequent admixture of the resulting solution of acid addition salt with a solvent of relatively low polarity, for example, diethyl ether or hexane, will usually cause precipitation of the acid addition salt. Either monoacid or diacid salts can be formed by using one or two equivalents, respectively, of the acid.

Acid addition salts of the Formula I pyrimidines can be transformed to other acid addition salts by a metathetical exchange of the original acid addition salt anion, e.g., the chloride ion, with another anion, for example, as described above with regard to the formation of penicillin salts.

In carboxyacylates of Formula V are produced by mixing a Formula I 1,2-dihydro-1-hydroxypyrimidine with the appropriate amount of a carboxyacylating agent, preferably in the presence of a diluent.

Although substantially any carboxyacylating agent can be used to produce these carboxyacylates, especially suitable are the anhydrides, mixed anhydrides, and acid chlorides of alkanoic, cycloalkanoic, alkenoic, cycloalkenoic, aralkanoic, aromatic, and heterocyclic carboxylic acids. These anhydrides and acid chlorides can also be substituted on any carbon but the carbonyl carbon with any of a wide variety of atomic or molecular moieties unreactive with the dihydropyrimidine reactants. Examples of such substituents are alkyl, e.g., methyl, butyl, decyl; alkoxy, e.g., methoxy, ethoxy, pentyloxy; alkylthio, e.g., methylthio, propylthio, heptylthio; dialkylamino, e.g., dimethylamino, diethylamino, dihexylamino; alkoxycarbonyl, e.g., methoxycarbonyl, propoxycarbonyl, nonoxycarbonyl; carboxyacyl, e.g., acetyl, butyryl; carboxamido, e.g., benzamido, acetamido; nitro; fluoro; cyano; and the like. Chlorine, bromine, and iodine can also be substituents on aromatic portions of the carboxyacylating agents.

Examples of suitable anhydrides are acetic anhydride, propionic anhydride, butyric anhydride, isobutyric anhydride, acrylic anhydride, crotonic anhydride, cyclohexanecarboxylic anhydride, benzoic anhydride, naphthoic anhydride, furoic anhydride, and the like, as well as the corresponding anhydrides substituted with one or more of the above-mentioned substituents. Examples of suitable acid chlorides are acetyl chloride, propionyl chloride, butyryl chloride, isobutyryl chloride, decanoyl chloride, acryloyl chloride, crotonoyl chloride, cyclohexanecarbonyl chloride, 3-cyclohexenecarbonyl chloride, phenylacetyl chloride, succinyl chloride, benzoyl chloride, naphthoyl chloride; furoyl chloride, 3-pyridinecarbonyl chloride, phthaloyl chloride, and the like, as well as the corresponding acid chlorides substituted with one or more of the above-mentioned substituents.

At least one molecular equivalent of carboxyacylating agent should be used for the introduction of each carboxyacyl moiety. When reactive carboxyacylating agents such as acetic anhydride are used, a diacyl compound is usually obtained even with only one molecular equivalent of carboxyacylating agent. In such cases, part of the dihydropyrimidine reactant does not form a carboxyacylate.

The carboxyacylation usually takes place rapidly in the range about $-20°$ to about $+50°$ C. Suitable diluents are ethers, e.g., diethyl ether and tetrahydrofuran; ketones, e.g., acetone and methyl ethyl ketone; esters, e.g., methyl acetate and ethyl acetate; acetonitrile; pyridine; and the like. The desired carboxyacylate often separates from the reaction mixture in crystalline form, and can be separated in the usual manner, for example, by filtration or centrifugation. Alternatively, the diluent can be evaporated, preferably at reduced pressure. The carboxyacylates can be purified by conventional techniques, for example by recrystallization from a suitable solvent or mixture of solvents.

The nature of each carboxyacylate depends on such factors as the nature of the dihydropyrimidine reactant, the nature and amount of carboxyacylating agent, the reaction time, and the reaction temperature. Usually a monoacylate or a diacylate, or a mixture of those, is obtained, although the formation of a triacylate is observed in some instances. The monoacylates are usually N-acyl compounds. The diacylates are either N,N'-diacyl or O,N-diacyl compounds. Use of the more reactive acylating agents, e.g., acetic anhydride, often results in N,N'-diacylates. The less reactive agents, e.g., benzoic anhydride, usually give N-acylates and/or O,N-diacylates.

Carboxyacylates produced at relatively low temperatures, i.e., about $-20°$ to about $0°$ C. and with relatively short reaction times, i.e., a few seconds to about 10 minutes, usually contain larger amounts of N-monoacylate and O,N-diacylate, and less N,N-diacylate, than those produced at higher temperatures, i.e., about $10°$ to about $50°$ C. and with longer reaction times, i.e., about 30 minutes to 100 hours.

Dihydropyrimidine carboxyacylates prepared as described above are easily transformed back to the Formula 1 dihydropyrimidine free base, preferably by warming with a lower alkanol, e.g., methanol or ethanol. Simultaneous treatment with a base, for example, gaseous ammonia, or an acid, for example, hydrochloric acid, usually accelerates the alcoholysis.

As mentioned above, the novel compounds of this invention, i.e., compounds of Formula 1, including the free bases and acid addition salts thereof, are useful as antihypertensive agents, antifertility agents, antiviral agents, antiinflammatory agents, and as central nervous system stimulants in the treatment of birds and mammals, including man. For those purposes, especially as antihypertensive agents, said novel compounds can be used in the nonprotonated (free base) form or in the protonated (acid addition salt) form either in association with a pharmaceutical carrier in solid or liquid dosage forms, such as tablets, capsules, powders, pills, granules, syrups, elixirs, suppositories, sterile aqueous or vegetable oil dispersions for parenteral use, and the like, alone or in combination with other drugs, for example, in combination with diuretics, sympathetic blocking agents, ganglion-blocking agents, peripheral vasodilators, reserpinoids, tranquilizers, sedatives, muscle relaxants, antihistamines and other antihypertensives.

Powders are prepared by comminuting the active ingredient to a suitable fine size and mixing with a similarly comminuted diluent. The diluent can be an edible carbohydrate material such as starch. Advantageously, a sweetening agent is present as well as a flavoring agent.

Capsules are produced by preparing a powder mixture as hereinbefore described and filling into formed gelatin sheets. Advantageously, as an adjuvant to the filling operation, a lubricant such as talc, magnesium stearate and calcium stearate is added to the powder mixture before the filling operation.

Tablets are made by preparing a powder mixture, granulating or slugging, adding a lubricant and pressing into tablets. The powder mixture is prepared by mixing the active ingredient suitably comminuted, with a diluent or base such as starch, lactose, kaolin, dicalcium phosphate, calcium sulfate, and the like. The powder mixture can be granulated by wetting with a binder such as syrup, gelatin solution, methylcellulose solution or acacia mucilage and forcing through a screen. As an alternative to wet granulating, the powder mixture can be slugged, i.e., run through a tablet machine and the resulting large tablets broken down into granules. The granules are further lubricated to prevent sticking to the tablet-forming dies by means of the addition of stearic acid, a stearate salt, talc, or mineral oil. The lubricated mixture is then compressed into tablets.

Advantageously, the tablet can be provided with a protective coating consisting of a sealing coat of shellac, a coating of sugar and methylcellulose, and a polish coating of carnauba wax.

Oral fluids are prepared in unit dosage forms such as syrups and elixirs wherein each teaspoonful of composition contains a predetermined amount of active ingredient for administration.

A syrup is prepared by dispersing the active ingredient in a suitably flavored aqueous sucrose solution. Similarly an elixir is prepared utilizing an aqueous-alcoholic vehicle. Elixirs are advantageous vehicles for use when a therapeutic agent, which is not sufficiently water-soluble, is in the composition.

For parenteral administration aqueous fluid unit dosage forms can be prepared. In preparing the parenteral form, a measured amount of active ingredient is placed in a vial, and the vial and its contents are sterilized and sealed. An accompanying vial of sterile water for injection is provided as a vehicle to form a dispersion prior to administration. Advantageously, the sterile water can have dissolved therein a local anesthetic and buffering agent. Parenteral aqueous solutions can also be made by utilizing a pharmacologically acceptable salt of the active ingredient, such as those mentioned above.

Alternatively, a parenteral suspension can be prepared by suspending the active ingredient in a parenterally acceptable vegetable oil with or without additional adjuvants, and sterilizing after filling into vials.

For veterinary oral use the active ingredient is conveniently prepared in the form of a food premix. The food premix can comprise the active ingredient in admixture with an edible pharmaceutical diluent such as starch, oatmeal, flour, calcium carbonate, talc, dried fish meal, and the like. The prepared premix is then conveniently added to the regular feed, thereby providing medication to the animal in the course of feeding.

The term "unit dosage form" as used in the specification and claims refers to physically discrete units suitable as unitary dosages for human subjects and animals, each unit containing a predetermined quantity of active material calculated to produce the desired therapeutic effect in association with the required pharmaceutical diluent, carrier or vehicle. The specifications for the novel unit dosage forms of this invention are dictated by and directly dependent on (a) the unique characteristics of the active material and the particular therapeutic effect to be achieved, and (b) the limitations inherent in the art of compounding such active material for therapeutic use in humans and animals, as disclosed in detail in the specification, these being features of the present invention. Examples of suitable unit dosage forms in accord with this invention are tablets, capsules, pills, powder packets, granules, wafers, cachets, suppositories, segregated multiples of any of the foregoing, and other forms as herein described.

The amount of active ingredient that is to be administered depends on the age, weight of the patient, the particular condition to be treated, the frequency of administration, and the route of administration. The dose range is from about 0. to about 30 mg. per kg. of body weight, preferably about 0.3 to about 10 mg. per kg. of body weight. The human dose ranges from about 5 to about 500 mg. daily given as a single dose or in 3 or 4 divided doses; preferably, the adult dose is from 25 to about 200 mg. Veterinary dosages will correspond to human dosages with amounts administered being in proportion to the weight of the animal as compared to adult humans.

The active ingredient is compounded with a suitable pharmaceutical diluent in unit dosage form, either alone or in combination with other active ingredients. The amount of such other active ingredients is to be determined with reference to the usual dosage of each such ingredient. Thus the novel compounds of the invention can be combined with other hypotensive agents such as $\alpha$-methyldopa 100–250 mg.; with diuretics such as aminophylline 100–200 mg., bendroflumethiazide 2.5–5 mg., hydrochlorothiazide 10–50 mg., trichloromethiazide 2–4 mg., triamterene 25–100 mg., ethoxzolamide 50–250 mg., amisometradine 200–400 mg., spironolactone 25–100 mg.; sympathetic blocking agents such as guanethidine sulfate 10–50 mg., bethanidine sulfate 5–20 mg.; ganglion-blocking agents, such as pentolinium bitartrate 20–200 mg., mecamylamine hydrochloride 2.5–5 mg., hexamethonium chloride 125–250 mg., chlorisondamine chloride 25–100 mg.; peripheral vasodilators such as hydralazine 10–100 mg., beta-pyridyl carbinol 50–150 mg., mebutamate 100–300 mg.; reserpine type drugs such as reserpine 0.1–1 mg., alseroxylon 2–4 mg., syrosingopine 0.5–2 mg., deserpidine 0.1–1 mg.; tranquilizers such as meprobamate 200–400 mg., ectylurea 100–300 mg., chlordiazepoxide hydrochloride 5–20 mg., promazine hydrochloride 25–150 mg., diazepan 2–10 mg.; sedatives such as phenobarbital 8–60 mg., methypyrlon 50–100 mg., amobarbital 20–40 mg., ethchlorvynol 100–200 mg.; muscle relaxants such as papaverine hydrochloride 20–100 mg., carisoprodol 200–400 mg., phenaglycodol 200–400 mg..

The invention can be more fully understood by the following examples.

EXAMPLE 1

6-Amino-1,2-dihydro-1-hydroxy-2-imino-4-(4-hydroxypiperidino)pyrimidine

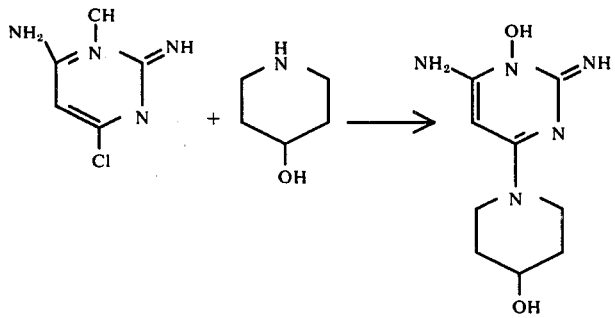

PART A-1

6-Amino-4-chloro-1,2-dihydro-1-hydroxy-2-iminopyrimidine

A 30 g. (0.15 mole) quantity of 4-chloro-2,6-diaminopyrimidine is dissolved in 600 ml. of hot 3A alcohol, the solution cooled to 0°–10° C. and 41.8 g. (0.24 mole) of m-chloroperbenzoic acid is added. The mixture is held at 0°–10° C. for 4 hours and filtered. The solid is shaken for 2 hours in 0.24 mole of 10% sodium hydroxide and filtered. The solid is washed with water and dried to yield 19.3 g. of crude product. This product is extracted for 1 hour with 900 ml. of boiling acetonitrile to yield 14.8 g. (44.7% yield) of 6-amino-4-chloro-1,2-dihydro-1-hydroxy-2-imino pyrimidine, m.p. 193° C.

Analysis: Calcd. for $C_4H_5ClN_4O$: C, 29.93; H, 3.14; Cl, 22.09; N, 34.90. Found: C, 30.60; H, 3.43; Cl, 22.26; N, 34.41.

PART B-1

6-Amino-1,2-dihydro-1-hydroxy-2-imino-4-(4-hydroxypiperidino)pyrimidine

A mixture of 3.0 g. 2,6-diamino-4-chloropyrimidine-N-oxide (Part A-1) and 21 g. 4-hydroxypiperidine is heated at 130° C. for 3 hours and then cooled. The excess 4-hydroxypiperidine is removed at 110° C./0.1 mm pressure. The residue is dissolved in methanol and passed through a column containing 50 g. Amberlite IRA-400 (a polystyrene quaternary ammonium anion exchange resin). The resulting methanolic solution is evaporated to dryness and the residue is dissolved in a mixture of methanol/acetone (1/10 by volume). On cooling a gummy material separates, is filtered and discarded. The solution is diluted with acetone until it becomes milky. It is then heated on a steam bath while the material clarifies and a solid begins to separate. After cooling the solid is filtered to give 2.5 g. of 6-amino-1,2-dihydro-1-hydroxy-2-imino-4-(4-hydroxypiperidino)pyrimidine, which darkens when heated to 236° C. and decomposes at 266°–267° C.

Analysis: Calcd. for $C_9H_{15}N_5O_2$: C, 47.99; H, 6.71; N, 31.09. Found: C, 48.06; H, 7.00; N, 31.18.

U.V. (ethanol): sh. 213 m$\mu$ ($\epsilon$ = 19,900); 230 m$\mu$ ($\epsilon$ = 34,400); 261 m$\mu$ ($\epsilon$ = 10,400); 286 m$\mu$ ($\epsilon$ = 11,000).

Mass spec. — M.W. = 225; peaks at 209, 166, 165, 164, 152

EXAMPLE 2

6-Amino-1,2-dihydro-1-hydroxy-2-imino-4-(3-hydroxypiperidino)pyrimidine

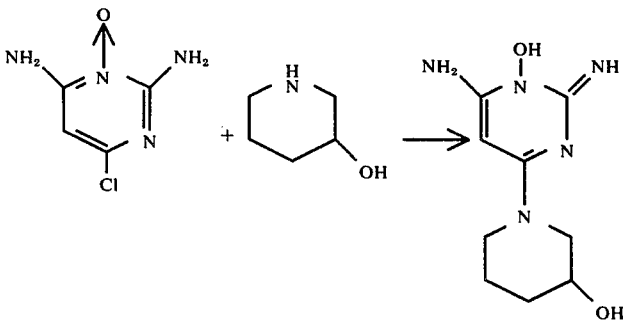

A mixture of 3.0 g. 2,6-diamino-4-chloropyrimidine-N-oxide and 21 g. 3-hydroxypiperidine is heated at 130° C. for 3 hours and then cooled. The cooled solution is diluted with a large volume chloroform. An oil separates, is decanted and dissolved in methanol. The solution is passed through a column containing 40 g. Amberlite IRA-400. The methanolic solution is evaporated and the residue is chromatographed on a column containing 300 g. silica gel (0.05–0.2 mesh) usng methanol/chloroform (1/1) as the solvent system. The elution from the column is halted when the effluent no longer gives a FeCl$_3$ color test. The solution is evaporated to dryness to yield a solid which is crystallized by heating in 160 ml. acetone and diluting the resulting solution with 25 ml. methanol. Filtration yields 2.0 g. of 6-amino-1,2-dihydro-1-hydroxy-2-imino-4-(3-hydroxypiperidino)pyrimidine, which darkens when heated to 236° C. and melts with decomposition at 266°–269° C.

Analysis: Calcd. for $C_9H_{15}N_5O_2$: C, 47.99; H, 6.71; N, 31.09. Found: C, 48.23; H, 6.27; N, 31.17.

U.V. (ethanol): sh. 213 mμ ($\epsilon$ = 20,450); 231 mμ ($\epsilon$ = 34,400); 262 mμ ($\epsilon$ = 10,600); 286 mμ ($\epsilon$ = 11,150).

Mass spec. — M.W. = 225; peaks at 209, 208, 207, 192, 191, 167, 165, 163.

EXAMPLE 3

6-Amino-1,2-dihydro-1-hydroxy-2-imino-4-(3,4-cis-dihydroxypiperidino)pyrimidine

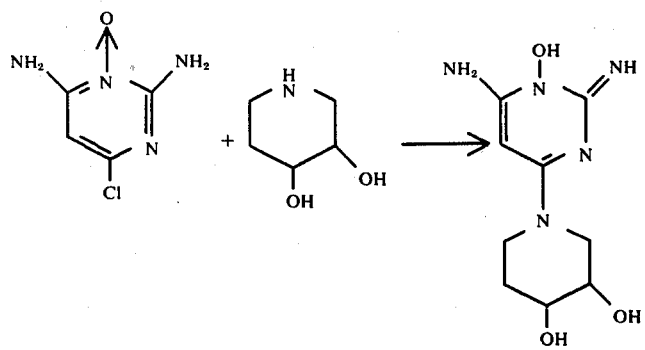

A mixture of 38 g. 3,4-cis-dihydroxypiperidine and 64 ml. of sodium methoxide solution (4.6 mM/ml) in 150 ml. methanol is shaken for 2 hours and filtered. To the solution is added 4.0 g. 2,6-diamino-4-chloropyrimidine-N-oxide and the mixture is heated at 130° C. for 4 hrs. The resulting solid slurry is extracted with sixteen 50 ml. portions of dimethoxyethane. The solid residue is dissolved in methanol, passed through a column containing 150 g. Amberlite IR-400 and the solvent is evaporated. The residue is chromatographed on a column containing 1000 g. silica (0.05–0.2 mesh) using methanol/chloroform (1/1) as the eluting solvent. All material giving a color test with ferric chloride is collected and the solvent is evaporated. The residue is crystallized six times by dissolving the solid in hot methanol and adding acetone until crystallization begins, to give 0.8 g. of pure 6-amino-1,2-dihydro-1-hydroxy-2-imino-4-(3,4-cis-dihydroxypiperidino)-pyrimidine.

Analysis: Calcd. for $C_9H_{15}N_5O_3$: C, 44.80; H, 6.27; N, 29.03. Found: C, 44.56; H, 6.47; N, 28.16.

U.V. (ethanol): end absorption; 230 mμ ($\epsilon$ = 36,950); 260 mμ ($\epsilon$ = 11,250); 285 mμ ($\epsilon$ = 11,900).

EXAMPLE 4

6-Amino-1,2-dihydro-1-hydroxy-2-imino-4-(3,4-trans-dihydroxypiperidino)pyrimidine

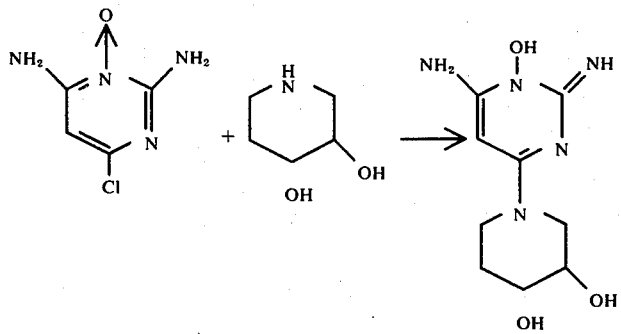

A mixture of 22.0 g. (0.14 M) 3,4-trans-dihydroxypiperidine and 31 ml. sodium methoxide solution (4.6 mM/ml., 0.14 M) in 100 methanol is shaken for 2 hours and filtered. To the solution is added 2.5 g. 2,6-diamino-4-chloropyrimidine-N-oxide and the mixture is heated at 135° C. for 20 hrs. The resulting solid slurry is extracted with 10 50-ml. portions of dimethoxyethane. The residue is dissolved in methanol and chromatographed over 400 g. silica (0.05–0.2 mesh) using methanol/chloroform (1/1) as the eluting solvent. The residue is chromatographed on a column containing 1000 g. silica (0.05–0.2 mesh) using methanol/chloroform (1/1) as the eluting solvent. All portions of the eluant which gives a color reaction with ferric chloride are combined and the solvent is evaporated. The residue is dissolved in hot methanol, treated with decolorizing charcoal, filtered and diluted, while hot, with acetone until solid begins to separate. After cooling the solid is filtered to yield 0.18 of 6-amino-1,2-dihydro-1-hydroxy-2-imino-4-(3,4-trans-dihydroxypiperidino)pyrimidine shown to be pure by thin layer chromatography.

Analysis: Strongly retains methanol solvate and elementary analyses are not meaningful.

U.V. (ethanol); sl sh. 213 mμ ($\epsilon$ = 25,300); 230 mμ ($\epsilon$ = 27,100); 259 mμ ($\epsilon$ = 7,900); 284 mμ ($\epsilon$ = 8,500).

Following the procedures of Examples 1 and 2 but in place of hydroxypyrimidine using ethanolamine, 3-amino-1-propanol, 2-amino-1-propanol, 1-amino-2-propanol, 1-amino-2-methyl-2-propanol, 3-amino-2-methyl-1-propanol, 2-amino-2-methyl-1-propanol, 3-amino-1-butanol, 4-amino-1-butanol, 3-amino-2-butanol, 4-amino-2-butanol, 1-amino-2-methyl-2- butanol, 1-amino-3-methyl-2-butanol, 1-amino-3-methyl-3-butanol, 2-amino-2-methyl-1-butanol, 2-amino-3-methyl-1-butanol, 3-amino-2-methyl-2-butanol, 4-amino-2-methyl-1-butanol, 1-amino-2-pentanol, 2-amino-1-pentanol, 3-amino-1-pentanol, 4-amino-1-pentanol, 5-amino-1-pentanol, 6-amino-1-hexanol; 2-amino-1,3-propanediol, 3-amino-1,2-propanediol, 2-amino-2-methyl-1,3-propanediol, 2-amino-1,3-butanediol, 2-amino-1,4-butanediol, 3-amino-1,5-pentanediol, 3-amino-1,2-pentanediol, 2-amino-2-ethyl-1,3-pentanediol, 2-amino-1-phenylethanol, 2-amino-1-phenyl-1,3-propanediol, 4-(aminomethyl)cyclohexanemethanol, 2-aminocyclopentanol, 3-aminocyclopentanol, 2-aminocyclohexanol, 2-amino-1,3-cyclohexanediol, 3-amino-1,2-cyclohexanediol, 3-aminocyclohexanol, 2-aminocycloheptanol, 3-aminocycloheptanol, 2-aminocyclooctanol, 4-aminocyclooctanol, 5-aminocyclooctanol, 2-methoxyethylamine, 2-ethoxyethylamine, 2-methoxy-1-methylethylamine, 2-ethoxy-1-methylethylamine, 2-methoxy-1,1,-dimethylethylamine, 2-propoxyethylamine, 2-isopropoxyethylamine, 1-methoxypropylamine, 2-ethoxypropylamine, 3-ethoxypropylamine, 2-methoxy-2-methylpropylamine, 3-methoxypropylamine, 3-isopropoxypropylamine, 1-(methoxymethyl)propylamine, 3-(2-methoxyethoxy)propylamine, 2-methoxybutylamine, 2-acetoxyethylamine, 2-acetoxy-1-methylethylamine, 2-(methylamino)ethanol, 2-(ethylamino)ethanol, 2-(isopropylamino)ethanol, 2-(propylamino)ethanol, 2-(butylamino)ethanol, 2-(t-butylamino)ethanol, 1-(methylamino)-2-propanol, 3-(methylamino)-1-propanol, 2-(methylamino)-1-propanol, 2-(methylamino)-1-butanol, 3-(methylamino)-1-butanol, 4-(methylamino)-1-butanol, 3-(methylamino)-1,2-propanediol, 1-[(2-hydroxyethyl)amino]-2-propanol, 1-(benzylamino)-2-propanol, 2-(benzylamino)-1-propanol, 3-(benzylamino)-1-propanol, N-benzylethanolamine, 2-(cyclohexylamino)ethanol, 2-(methylamino)cyclopentanol, 3-(methylamino)cyclopentanol, 2-[(2-methoxyethyl)amino]ethanol, 1-(2-methoxyethylamino)-2-propanol, methylaminoacetaldehyde dimethylacetal, N,N-bis-(2,2'-diethoxyethyl)amine, 2-aziridinemethanol, 1-(2-aziridine)ethanol, 3-methyl-2-aziridinemethanol, 3-azetidinol, 3-pyrrolidinol, 3,4-pyrrolidinediol, 2-pyrrolidinemethanol, 3-pyrrolidinemethanol, 2,5-pyrrolidinedimethanol, 3-piperidinol, 4-piperidinol, 3,4-cis-piperidinediol, 3,4-trans-piperidinediol, 4-methyl-4-piperidinol, 2,2,6,6-tetramethyl-4-piperidinol, 3-piperidinemethanol, 2-piperidinemethanol, 4-hydroxy-4-piperidinemethanol, 2-(2-piperidine)ethanol, 1-(3-piperidine)ethanol, 3,5-piperidinedimethanol, 2,6-piperidinedimethanol, 4-hydroxyhexamethyleneimine, 2-hydroxymethylhexamethyleneimine, 4-hydroxyheptamethyleneimine, 5-hydroxyheptamethyleneimine, 4-hydroxyoctamethyleneimine, 3-methyl-3-morpholinemethanol, 2,3-dimethyl-3-morpholinemethanol, 2,3,3,5-tetramethyl-2-morpholinol, 4-methyl-2-piperazinemethanol, 2-(2-piperazine)ethanol, 2-(methoxymethyl)aziridine, 2-methyl-3-methoxyazetidine, 3,5-dimethyl-3-methoxypyrrolidine, 3-methoxypiperidine, 4-ethoxypiperidine, 4-methyl-4-propoxypiperidine, 4-(butoxyethyl)piperidine, 2-methoxy-6-methylmorpholine, 2-methyl-2-(acetoxymethyl)aziridine, 3-acetoxy-4-methylpyrrolidine, 3-acetoxypiperidine, 4-acetoxypiperidine, and 4-propionoxypiperidine, there are obtained 6-amino-1-hydroxy 4-$R_1$-2-imino-1,2-dihydropyrimidines in which $R_1$ are as follows: 2-hydroxyethylamino, 3-hydroxypropylamino, 2-hydroxy-1-methylethylamino, 2-hydroxypropylamino, 2-hydroxy-2-methylpropylamino, 3-hydroxy-2-methylpropylamino, 2-hydroxy-1,1-dimethylethylamino, 3-hydroxy-1-methylpropylamino, 4-hydroxy-butylamino, 2-hydroxy-1,2-dimethylethylamino, 3-hydroxybutylamino, 2-hydroxy-2-methylbutylamino, 2-hydroxy-3-methylbutylamino, 3-hydroxy-3-methylbutylamino, 2-hydroxy-1-ethyl-1-methylethylamino, 1-hydroxymethyl-2-methylpropylamino, 2-hydroxy-1,2-dimethylpropylamino, 4-hydroxy-3-methylbutylamino, 2-hydroxypentylamino, 1-hydroxymethylbutylamino, 3-hydroxy-1-ethylpropylamino, 4-hydroxy-1-methylbutylamino, 5-hydroxypentylamino, 6-hydroxyhexylamino, dihydroxymethylmethylamino, 2,3-dihydroxypropylamino, 1,1-dihydroxymethylethylamino, 2-hydroxy-1-hydroxymethylpropylamino, 3-hydroxy-1-hydroxymethylpropylamino, bis-2-hydroxyethylmethylamino, 1-ethyl-2,3-dihydroxypropylamino, 1-ethyl-1-hydroxymethyl-2-hydroxybutylamino, 2-hydroxy-2-phenylethylamino, 2-hydroxy-1-hydroxymethyl-2-phenylethylamino, 4-hydroxymethylcyclohexylmethylamino, 2-hydroxycyclopentylamino, 3-hydroxycyclopentylamino, 2-hydroxycyclohexylamino, 2,6-dihydroxycyclohexylamino, 2,3-dihydroxycyclohexylamino, 3-hydroxycyclohexylamino, 2-hydroxycycloheptylamino, 3-hydroxycycloheptylamino, 2-hydroxycyclooctylamino, 4-hydroxycyclooctylamino, 5-hydroxycyclooctylamino, 2-methoxyethylamino, 2-ethoxyethylamino, 2-methoxy-1-methylethylamino, 2-ethoxy-1-methylethylamino, 2-methoxy-1,1-dimethylethylamino, 2-propoxyethylamino, 2-isopropoxyethylamino, 1-methoxypropylamino, 2-ethoxypropylamino, 3-ethoxypropylamino, 2-methoxy-2-methylpropylamino, 3-methoxypropylamino, 3-isopropoxypropylamino, 1-(methoxymethyl)propylamino, 3-(2-methoxyethoxy)propylamino, 2-methoxybutylamino, 2-acetoxyethylamino, 2-acetoxy-1-methylethylamino, (N-hydroxyethyl-N-methylamino), (N-2-hydroxyethyl-N-ethylamino), (N-2-hydroxyethyl-N-isopropylamino), (N-2-hydroxyethyl-N-propylamino), (N-2-hydroxyethyl-N-butylamino), (N-2-hydroxyethyl-N-tert-butylamino), (N-2-hydroxypropyl-N-methylamino), (N-3-hydroxypropyl-N-methylamino), (N-2-hydroxy-1-methylethyl-N-methylamino), (N-1-hydroxymethylpropyl-N-methylamino), (N-3-hydroxy-1-methylpropyl-N-methylamino), (N-4-hydroxybutyl-N-methylamino), (N-2,3-dihydroxypropyl-N-methylamino), (N-2-hydroxyethyl-N-2-hydroxypropylamino), (N-benzyl-N-2-hydroxypropylamino), (N-benzyl-N-2-hydroxy-1-methylethylamino), (N-benzyl-N-3-hydroxypropylamino), (N-benzyl-N-2-hydroxyethylamino), (N-cyclohexyl-N-2-hydroxyethylamino), (N-2-hydroxycyclopentyl-N-methylamino), (N-3-hydroxycyclopentyl-N-methylamino), (N-2-hydroxyethyl-N-2-methoxyethylamino), (N-2-hydroxypropyl-N-2-methoxyethylamino), (N-methylamino-N-2,2-dimethoxyethylamino), N,N-bis(2,2'-diethoxyethyl)amino, 2-hydroxymethylaziridino, 1-hydroxyethylaziridino, (2-hydroxymethyl-3-methylaziridino), 3-hydroxyacetidino, 3-hydroxypyrrolidino, 3,4-dihydroxypyrrolidino, 2-hydroxymethylpyrrolidino, 3-hydroxymethylpyrrolidino, (2,5-dihydroxymethylpyrrolidino), 3-hydroxypiperidino, 4-hydroxypiperidino, 3,4-cis-dihydroxypiperidino, 3,4-trans-dihydroxypiperidino, 4-hydroxy-4-methylpiperidino, 4-hydroxy-2,2,6,6-tetramethylpiperidino, 3-hydroxymethylpiperidino, 2-hydroxymethylpiperidino, 4-hydroxy-4-hydroxymethylpiperidino, [2-(2-hydroxyethyl)piperidino], [3-(1-hydroxyethyl)piperidino], (3,5-dihydroxymethylpiperidino), 2,6-dihydroxymethylpiperidino, 4-hydroxyhexamethyleneimino, 2-hydroxymethylhexamethyleneimino, 4-hydroxyheptamethyleneimino, 5-hydroxyheptamethyleneimino, 4-hydroxyoctamethyleneimino, 3-hydroxymethyl-3-methylmorpholino, 3-hydroxymethyl-2,3-dimethylmorpholino, 2-hydroxy-2,3,3,5-tetramethylmoropholino, 2-hydroxymethyl-4-methylpiperazino, 2-(2-hydroxyethyl)piperazino, 2-(methoxymethyl)aziridino, 2-methyl-3-methoxyazetidino, 3,5-dimethyl-3-methoxypyrrolidino, 3-methoxypiperidino, 4-ethoxypiperidino, 4-methyl-4-propoxypiperidino, 4-(butoxyethyl)piperidino, 2-methoxy-6-methylmoropholino, 2-methyl-3-(acetoxymethyl)aziridino, 3-acetoxy-4-methylpyrrolidino, 3-acetoxypiperidino, 4-acetoxypiperidino, 4-propionoxypiperidino.

EXAMPLE 5

Tablets 20,000 Scored tablets for oral use, each containing 200 mg. of 6-amino-1,2-dihydro-1-hydroxy-2-imino-4-(3- or 4-hydroxypiperidino)pyrimidine free base are prepared from the following ingredients:

| | |
|---|---|
| 6-amino-1,2-dihydro-1-hydroxy-2-imino-4-(3- or 4-hydroxy-piperidino)pyrimidine, micronized | 4000 g. |
| Starch, U.S.P. | 350 g. |
| Talc, U.S.P. | 250 g. |
| Calcium stearate | 35 g. |

The micronized 6-amino-1,2-dihydro-1-hydroxy-2-imino-4-(3- or 4-hydroxypiperidino)pyrimidine free base is graulated with a 4 percent w./v. aqueous solution of methylcellulose U.S.P. (1500 cps.). To the dried granules is added a mixture of the remainder of the ingredients and the final mixture is compressed into tablets of proper weight. Satisfactory clinical response is obtained in adults showing hypertension with 1 tablet which can be repeated in 4 hours, if necessary. For moderate conditions, a half tablet is used.

EXAMPLE 6

Capsules 20,000 Two-piece hard gelatin capsules for oral use, each containing 100 mg. of 6-amino-1,2-dihydro-1-hydroxy-2-imino-4-(3- or 4-hydroxypiperidino)pyrimidine free base are prepared from the following ingredients:

| | |
|---|---|
| 6-amino-1,2-dihydro-1-hydroxy-2-imino-4-(3- or 4-hydroxy-piperidino)pyrimidine | 2000 g. |
| Lactose, U.S.P. | 1000 g. |
| Starch, U.S.P. | 300 g. |
| Talc, U.S.P. | 65 g. |
| Calcium stearate | 25 g. |

The micronized 6-amino-1,2-dihydro-1-hydroxy-2-imino-4-(3- or 4-hydroxypiperidino)pyrimidine free base is mixed with the starch-lactose mixture followed by the talc and calcium stearate. The final mixture is then encapsulated in the usual manner. One capsule is used every 3 hours to control hypertension.

Capsules containing 10, 25, 50 and 350 mg. of 6-amino-1,2-dihydro-1-hydroxy-2-imino-4-(3- or 4-hydroxypiperidino)pyrimidine free base are also prepared by substituting 200, 500, 1000 and 7000 g. for 2000 g. in the above formulation.

EXAMPLE 7

Soft elastic capsules

One piece soft elastic capsules for oral use, each containing 5 mg. of 6-amino-1,2-dihydro-1-hydroxy-2-imino-4-(3- or 4-hydroxypiperidino)pyrimidine free base are prepared in the usual manner by first dispersing the powdered active material in sufficient corn oil to render the material capsulatable.

EXAMPLE 8

Aqueous preparation

An aqueous preparation for oral use containing in each 5 ml., 50 mg. of 6-amino-1,2-dihydro-1-hydroxy-2-imino-4-(3- or 4-hydroxypiperidino)pyrimidine hydrochloride is prepared from the following ingredients:

| | |
|---|---|
| 6-amino-1,2-dihydro-1-hydroxy-2-imino-4-(3- or 4-hydroxy-piperidino)pyrimidine hydrochloride | 100 g. |
| Methylparaben, U.S.P. | 7.5 g. |
| Propylparaben, U.S.P. | 2.5 g. |
| Saccharin sodium | 12.5 g. |
| Cyclamate sodium | 2.5 g. |
| Glycerin | 3000 ml. |
| Tragacanth powder | 10 g. |
| Orange oil flavor | 10 g. |
| F. D. and C. orange dye | 7.5 g. |
| Deionized water, q.s. to | 10,000 ml. |

EXAMPLE 9

Parenteral suspension

A sterile aqueous suspension suitable for intramuscular injection and containing in each milliliter, 25 mg. of 6-amino-1,2-dihydro-1-hydroxy-2-imino-4-(3- or 4-hydroxypiperidino)pyrimidine free base is prepared from the following ingredients:

| | |
|---|---|
| Polyethylene glycol 4000, U.S.P. | 3 g. |
| Sodium chloride | 0.9 g. |
| Polysorbate 80, U.S.P. | 0.4 g. |
| Sodium metabisulfite | 0.1 g. |
| Methylparaben, U.S.P. | 0.18 g. |
| Propylparaben, U.S.P. | 0.02 g. |
| 6-amino-1,2-dihydro-1-hydroxy-2-imino-4-(3- or 4-hydroxy-piperidino)pyrimidine free base (micronized) | 2.5 g. |
| Water for injection, q.s. to | 100 ml. |

EXAMPLE 10

Aqueous solution

An aqueous solution for oral use and containing in each 5 ml., 25 mg. of 6-amino-1,2-dihydro-1-hydroxy-2-imino-4-(3- or 4-hydroxypiperidino)pyrimidine hydrochloride is prepared from the following ingredients:

| | |
|---|---|
| 6-amino-1,2-dihydro-1-hydroxy-2-imino-4-(3- or 4-hydroxy-piperidino)pyrimidine hydrochloride | 5 g. |
| Deionized water, q.s. to | 1000 ml. |

EXAMPLE 11

Parenteral solution

A sterile aqueous solution for intravenous or intramuscular injection and containing 20 mg. of 6-amino-1,2-dihydro-1-hydroxy-2-imino-4-(3- or 4-hydroxypiperidino)pyrimidine maleate in each 2 ml. is prepared from the following ingredients:

| | |
|---|---|
| 6-amino-1,2-dihydro-1-hydroxy-2-imino-4-(3- or 4-hydroxy-piperidino)pyrimidine maleate | 10 g. |
| Chlorobutanol | 3 g. |
| Water for injection, q.s. to | 1000 ml. |

EXAMPLE 12

Capsules

One thousand hard gelatin capsules for oral use, each containing 25 mg. of 6-amino-1,2-dihydro-1-hydroxy-2-imino-4-(3- or 4-hydroxypiperidino)pyrimidine free base and 25 mg. of hydrochlorothiazide are prepared from the following ingredients:

| | |
|---|---|
| 6-amino-1,2-dihydro-1-hydroxy-2-imino-4-(3- or 4-hydroxy-piperidino)pyrimidine free base micronized | 25 g. |
| Hydrochlorothiazide | 25 g. |
| Starch | 125 g. |
| Talc | 25 g. |
| Magnesium stearate | 15 g. |

One capsule 2 to 4 times a day is advantageous in the relief of moderate to severe hypertension in adult humans.

EXAMPLE 13

Capsules

One thousand hard gelatin capsules for oral use, each containing 50 mg. of 6-amino-1,2-dihydro-1-hydroxy-2imino-4-(3- or 4-hydroxypiperidino)pyrimidine free base, 25 mg. of hydrochlorothiazide, 0.1 mg. of reserpine, and 400 mg. of potassium chloride are prepared from the following ingredients:

| | |
|---|---|
| 6-amino-1,2-dihydro-1-hydroxy-2-imino-4-(3- or 4-hydroxy-piperidino)pyrimidine free base micronized | 50 g. |
| Hydrochlorothiazide | 25 g. |
| Reserpine | 0.1 g. |
| Potassium chloride | 400 g. |
| Talc | 75 g. |
| Magnesium stearate | 20 g. |

One or two capsules daily is advantageously used for reducing hypertension.

EXAMPLE 14

Tablets

Ten thousand tablets for oral use, each containing 50 mg. of 6-amino-1,2-dihydro-1-hydroxy-2-imino-4-(3- or 4-hydroxypiperidino)pyrimidine free base and 25 mg. of chlorisondamine chloride, are prepared from the following ingredients:

| | |
|---|---|
| 6-amino-1,2-dihydro-1-hydroxy-2-imino-4-(3- or 4-hydroxy-piperidino)pyrimidine free base | 500 g. |
| Chlorisondamine chloride | 250 g. |
| Lactose | 1200 g. |
| Corn starch | 500 g. |
| Talc | 500 g. |
| Calcium stearate | 25 g. |

The powdered ingredients are thoroughly mixed and slugged. The slugs are broken down into granules which are then compressed into tablets. For relief of hypertension in adult humans, 1 tablet is administered 1 to 4 times daily after meals.

EXAMPLE 15

Tablets

Ten thousand scored tablets for oral use, each containing 25 mg. of 6-amino-1,2-dihydro-1-hydroxy-2-imino-4-(3- or 4-hydroxypiperidino)pyrimidine free base and 0.1 mg. of reserpine, are prepared from the following ingredients and using the procedure of Example 14.

| | |
|---|---|
| 6-amino-1,2-dihydro-1-hydroxy-2-imino-4-(3- or 4-hydroxy-piperidino)pyrimidine free base | 250 g. |
| Reserpine | 1 g. |
| Lactose | 1500 g. |
| Corn starch | 500 g. |
| Talc | 500 g. |
| Calcium stearate | 25 g. |

This combination of active materials is effective in adult humans for the reduction of hypertension. The dose is one-half to two tablets 3 times a day depending on the severity of the condition.

EXAMPLE 16

Capsules

Ten thousand hard gelatin capsules for oral use, each containing 25 mg. of 6-amino-1,2-dihydro-1-hydroxy-2-imino-4-(3- or 4-hydroxypiperidino)pyrimidine free base and 200 mg. of meprobamate, are prepared from the following ingredients:

| | |
|---|---|
| 6-amino-1,2-dihydro-1-hydroxy-2-imino-4-(3- or 4-hydroxy-piperidino)pyrimidine free base | 250 g. |
| Meprobamate | 2000 g. |
| Starch | 350 g. |
| Talc | 250 g. |
| Calcium stearate | 150 g. |

One capsule 4 times a day is useful in the treatment of hypertension.

EXAMPLE 17

Tablets

Ten thousand tablets for oral use, each containing 25 mg. of 6-amino-1,2-dihydro-1-hydroxy-2-imino-4-(3- or 4-hydroxypiperidino)pyrimidine free base and 40 mg. of ethoxzolamide, are prepared from the following ingredients:

| | |
|---|---|
| 6-amino-1,2-dihydro-1-hydroxy-2-imino-4-(3- or 4-hydroxypiperidino)pyrimidine free base | 250 g. |
| Ethoxzolamide | 400 g. |
| Lactose | 1200 g. |
| Corn starch | 500 g. |
| Talc | 500 g. |
| Calcium stearate | 25 g. |

The powdered ingredients are thoroughly mixed and slugged. The slugs are broken into granules which are then compressed into tablets. For relief of hypertension in adult humans, 1 tablet is administered 2 to 4 times daily.

We claim:

1. A compound of the formula:

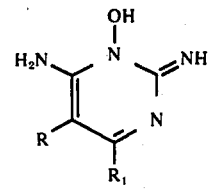

where R is hydrogen or lower alkyl and $R_1$ is piperidino having attached as substituents on carbon atoms thereof 0 to 3 lower alkyl, inclusive, and in addition 1 or 2 hydroxy or lower acyloxy groups selected from the group consisting of acetoxy and propionoxy, the free base form or an acid addition salt selected from the group consisting of hydrochloric, hydrobromic, maleic, and pamoic.

2. A compound according to claim 1 where R is hydrogen, $R_1$ is a substituted piperidino substituent selected from the group consisting of 4-hydroxypiperidine, 3-hydroxypiperidine, 4-methyl-4-hydroxypiperidine, 3-acetoxypiperidine, 4-acetoxypiperidine, and 4-propionoxypiperidine, and where the acid addition salt is hydrochloric or maleic.

3. A compound according to claim 2 wherein $R_1$ is 3-hydroxypiperidino and R is hydrogen.

4. A compound according to claim 2 wherein $R_1$ is 4-hydroxypiperidino and R is hydrogen.

* * * * *

UNITED STATES PATENT AND TRADEMARK OFFICE
CERTIFICATE OF CORRECTION

PATENT NO. : 3,998,827

DATED : December 21, 1976

INVENTOR(S) : Richard C. Thomas, et al.

It is certified that error appears in the above—identified patent and that said Letters Patent is hereby corrected as shown below:

Column 1, line 35: "lower hydroxy," should read -- lower hydroxy-, --.
Column 4, line 38: "carboxylates" should read -- carboxyacylates --.
Column 4, line 61: "are are" should read -- and are --.
Column 6, lines 49-50: "4-(n:butoxyethyl)" should read -- 4-(n-butoxyethyl) --.
Column 7, line 38: "In" should read -- The --.
Column 10, line 32: "about 0." should read -- about 0.1 --.
Column 11, Example 1, first drawing of the formula:

" 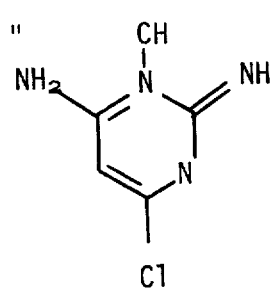  "   should read --  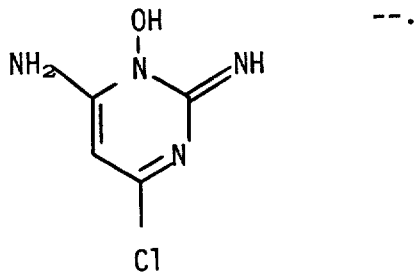  --.

Column 12, line 61: "usng" should read -- using --.

UNITED STATES PATENT AND TRADEMARK OFFICE
CERTIFICATE OF CORRECTION

PATENT NO. : 3,998,827

DATED : December 21, 1976

INVENTOR(S) : Richard C. Thomas, et al.

It is certified that error appears in the above—identified patent and that said Letters Patent is hereby corrected as shown below:

Column 17, line 11: "2,3,3,5-tetramethylmorpholino," should read -- 2,3,3,5-tetramethylmorpholino, --.
Column 19, line 51: "2imino-" should read -- 2-imino- --.
Column 22, line 22, Claim 2: "hydroxypiperdine" should read -- hydroxypiperidine --.

Signed and Sealed this

Fourth Day of August 1981

[SEAL]

Attest:

Attesting Officer

GERALD J. MOSSINGHOFF

Commissioner of Patents and Trademarks